United States Patent [19]

Mookherjee et al.

[11] Patent Number: 5,008,437

[45] Date of Patent: Apr. 16, 1991

[54] SCHIFF BASE REACTION PRODUCT OF ETHYL VANILLIN AND METHYL ANTHRANILATE AND ORGANOLEPTIC USES THEREOF

[75] Inventors: Braja D. Mookherjee, Holmdel; Robert W. Trenkle, Point Pleasant, both of N.J.; Nicholas Calderone, Laurel Hollow, N.Y.; Ronald S. Fenn, New Providence, N.J.

[73] Assignee: International Flavors & Fragrances Inc., New York, N.Y.

[21] Appl. No.: 588,737

[22] Filed: Sep. 27, 1990

Related U.S. Application Data

[62] Division of Ser. No. 134,978, Dec. 18, 1987, abandoned.

[51] Int. Cl.⁵ .................................. C07C 229/00
[52] U.S. Cl. ........................................... 560/35
[58] Field of Search ................................. 560/35

[56] References Cited

U.S. PATENT DOCUMENTS 4,177,170  12/1979  Cookson et al. ................. 252/522
4,639,330   1/1987  Sprecker et al. ............. 252/174.11

Primary Examiner—Bruce Gray
Attorney, Agent, or Firm—Arthur L. Liberman

[57] ABSTRACT

Described is the schiff base reaction product of methyl anthranilate having the structure:

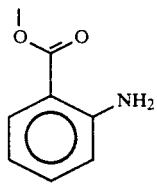

with ethyl vanillin having the structure:

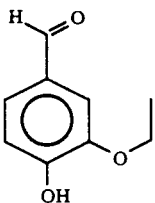

a compound having the structure:

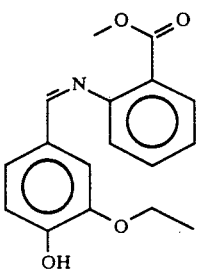

and uses thereof in augmenting or enhancing the aroma of perfume compositions, perfumed articles including perfumed polymers and colognes. The schiff base having the structure:

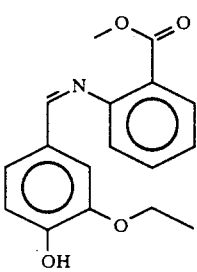

also has unexpected, unobvious and advantageous utilities for its deodorancy properties in addition to having valuable properties as a fragrance material.

2 Claims, 4 Drawing Sheets

GLC PROFILE FOR EXAMPLE I.

MASS SPECTRUM FOR EXAMPLE I

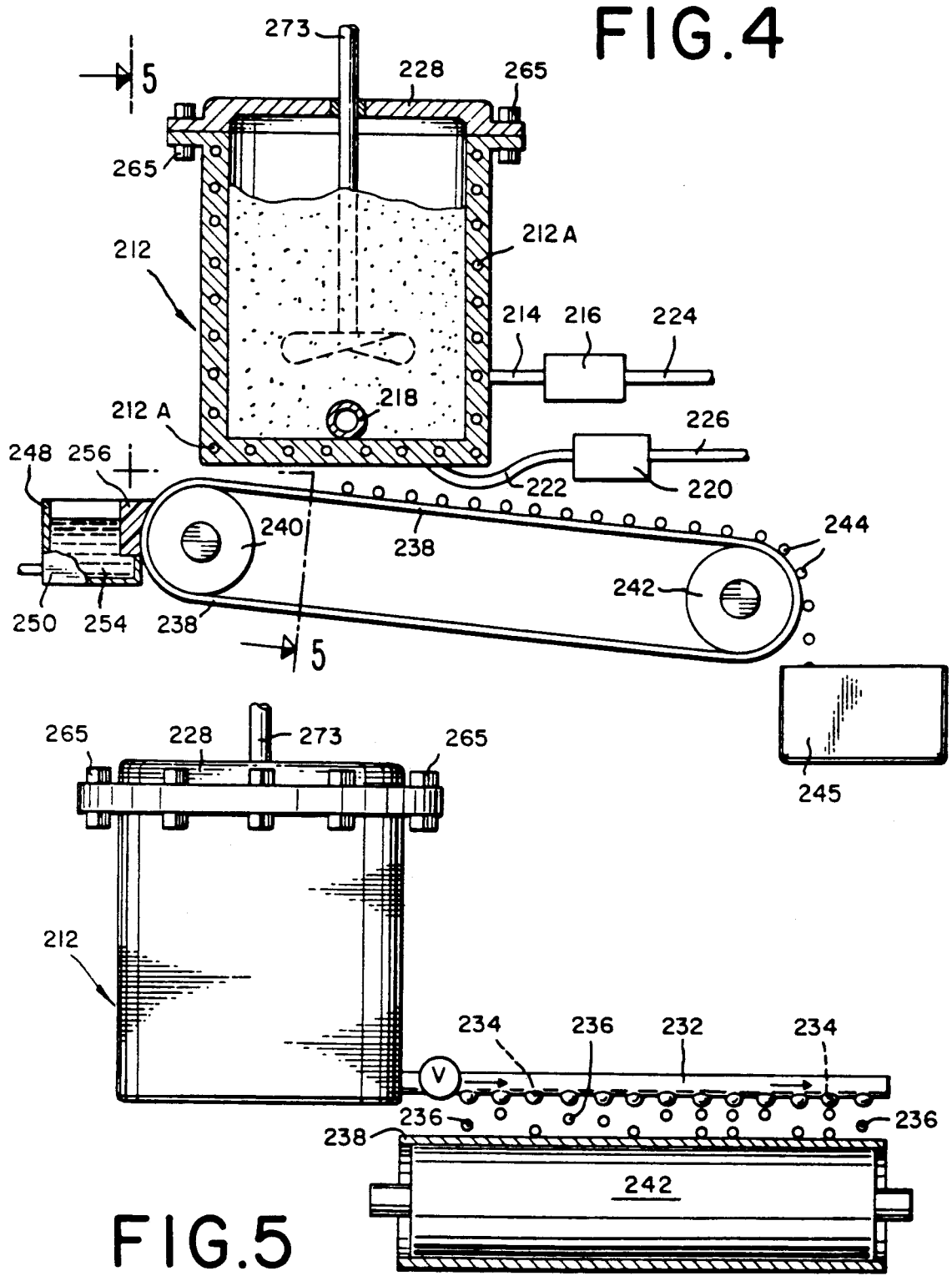

SCHIFF BASE REACTION PRODUCT OF ETHYL VANILLIN AND METHYL ANTHRANILATE AND ORGANOLEPTIC USES THEREOF

This is a divisional of application Ser. No. 134,978, filed 12/18/87 now abandoned.

BACKGROUND OF THE INVENTION

Our invention relates to the novel reaction product which is the schiff base of ethyl vanillin and methyl anthranilate, the compound having the structure:

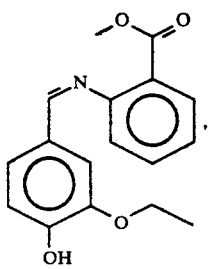

and the organoleptic use thereof in augmenting or enhancing the aroma of perfume compositions, colognes and perfumed articles and in enhancing or augmenting the effect of deodorancy; as a maskant for malodors emanating from the axillary regions of mammalian species.

Inexpensive chemical compositions of matter which can provide sweet, vanilla bean-like and sassafras aroma profiles with sweet topnotes and which are highly substantive and long-lasting are highly desirable in the art of perfumery. Many of the natural materials which provide such fragrances and contribute desired nuances to perfumery compositions as well as perfumed articles including solid or liquid anionic, cationic, nonionic or zwitterionic detergents, fabric softener compositions and fabric softener articles are high in cost, vary in quality from one batch to another and/or are generally subject to the usual variations of natural products.

Still more desirable are materials which can both provide useful fragrance effects including high substantivity and a long-lasting fragrance and also provide a deodorancy effect whereby malodors can be masked by means of the use of the compound in, for example, the axillary regions of mammalian species including human beings.

Reaction products of carbonyl-containing compounds and amine-containing compounds are well known in the art of flavoring and in the art of of perfumery. Thus, U.S. Pat. No. 4,618,501 issued on Oct. 21, 1986 discloses the flavoring of foodstuffs with alpha,-beta-keto-amines and states that an alpha,beta-keto-amine having a nutty corn, cereal aroma may be used for flavoring compositions for foods having the structure:

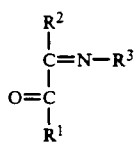

wherein $R_1$, $R_2$ and $R_3$ are selected from the group consisting of a saturated or unsaturated alkyl straight or branched chain hydrocarbons having from 1-3 carbon atoms.

U.S. Pat. No. 3,625,710 issued on Dec. 7, 1971 discloses the use of aldimines as chocolate-like flavors which aldimines are resulting from the reaction product of amines and aldehydes, for example, N-isobutylidenefurfurylamine, N-isopentylidenefurfurylamine, N-isopentylideneisopentylamine.

Schiff bases are also well known in the art of perfumery. Thus, for example, Chemical Abstracts Volume 103, 1985, No. 123134z (Abstract of Japan Kokai No. 60/78951 discloses the use in perfumery of compounds having the structure:

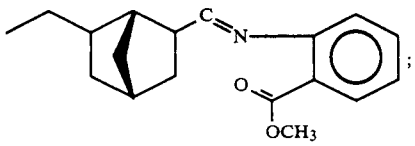

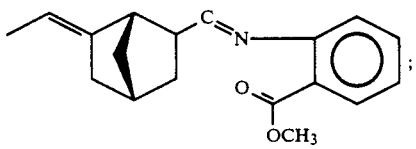

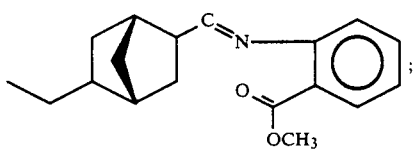

and

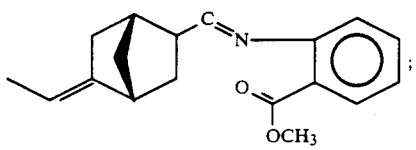

Arctander "Perfume and Flavor Chemicals (Aroma Chemicals)", Volume II, published by the Author in 1969 discloses the organoleptic properties of the schiff base of methyl anthranilate and vanillin having the structure:

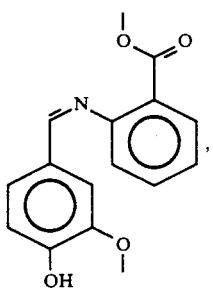

thusly:

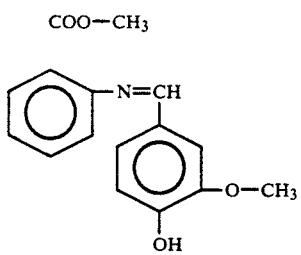

$C_{16}H_{15}NO_4 = 285.30$

Viscous, dark-yellowish liquid, occasionally with an orange-reddish tint, or an olive-green color.

Insoluble in water, soluble in alcohol and oils.

Intensely sweet, balsamic-floral odor of very good tenacity. The odor varies considerably from one sample (supplier) to another, a fact which is often observed in "Schiff's bases". Generally, a mild surplus of the aldehyde component is preferable, except in cases of very pungent aldehydes such as Cuminaldehyde, Cinnamic aldehyde, Methylcinnamic aldehyde, etc.

The title material has very little use in perfumes, and is simply missing from most perfume laboratories. It may be considered as a curiosity, more than a practical perfume material, but it is briefly mentioned in this work because it may often "occur" in a perfume, since the use of Vanillin and Methylanthranilate in the same composition is not a very rare or unusual case. The addition of Vanillin directly into Methylanthranilate may often cause a strong coloring, brown or orange, of the mixture, and it is recommended not to add these materials in sequence, one next to the other.

Among scores of suggested "Schiff's bases", only very few have become standard perfume items, and the title material is not one of them. But it is classified as "interesting", by some perfumers.

Prod.: by condensation of Vanillin with Methylanthranilate in molecular proportions, preferably in a suitable diluent to prevent violent darkening, and to render the final product more pourable, handy for use.

Arctander also discloses the organoleptic properties of vanillin-ethyl carbonate-phenetidine, thusly:

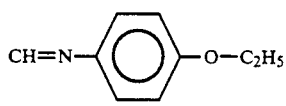
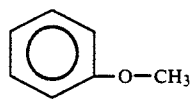

$C_{19}H_{21}NO_5 = 343.39$

Yellowish needle-like crystals. M.P. 88° C.

Very slightly soluble in water, moderately soluble in alcohol, soluble in hot alcohol and oils.

The title material is briefly mentioned because it behaves in a rather peculiar manner. Although it has an unquestionable odor of Vanillin-type, rather soft, but quite pleasant and not exactly weak, its aqueous solution or the dry material itself has hardly any taste at all.

This peculiarity has not been explained in literature, but it could well be that the material (molecule), part of which is an aromatic aminoether, has mildly anaesthetic effect upon the human mucous membranes. Many members of this chemical series have anaesthetic effect.

The material was developed many decades ago for pharmaceutical purposes, but was also introduced to the perfume and flavor industry at that time. It has no longer importance to perfumes or flavors, but it is still used in pharmacy.

The compound of our invention having the structure:

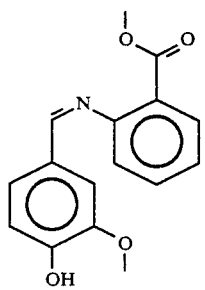

has unexpected, unobvious and advantageous organoleptic properties including deodorancy properties as opposed to the compounds of the prior art including the compound having the structure:

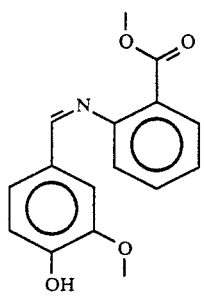

The book "Flavor & Fragrance Materials-1987" published by Allured Publishing Corporation, P. O. Box 318, Wheaton, Ill. 60189-0318 discloses on page 154 the commercial availability of the following schiff bases:

Methyl anthranilate and amyl cinnamic aldehyde;
Methyl anthranilate and hydroxy citronellal;
Methyl anthranilate and lilial;
Methyl anthranilate and anisic aldehyde;
Methyl anthranilate and decanal;
Methyl anthranilate and lyral;
Methyl anthranilate and iso-nonylaldehyde;
Methyl anthranilate and phenylacetaldehyde.

Schiff bases are also known to be useful as intermediate in producing other fragrance materials. Thus, U.S. Pat. No. 3,898,283 issued on Aug. 5, 1975 discloses novel schiff base intermediates used in producing 4 or 5 phenylpentenals having the structure:

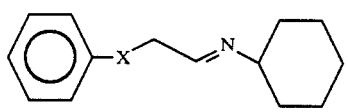

wherein X is from the group consisting of:

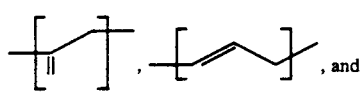

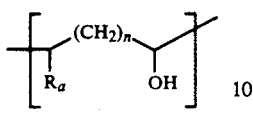

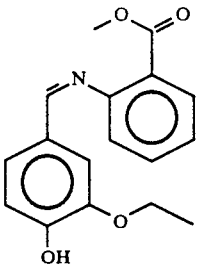

and wherein $R_a$ is hydrogen or methyl.

Nothing in the prior art however discloses the novel reaction products or reaction product mixtures of our invention having unobvious, unexpected and advantageous organoleptic properties.

Indeed, nothing in the prior art is indicative of the novel schiff base reaction products of our invention having deodorizing properties that is, having a deodorant value of 0.50 up to 3.5 as measured by the deodorant value test described in U.S. Pat. No. 4,304,679 incorporated by reference herein or having a Lipoxidase-inhibiting capacity of at least 50% and a Malodour reduction value of from 0.25 up to 3 as measured by the Malodour reduction value test disclosed in U.S. Pat. No. 4,663,068 incorporated by reference herein.

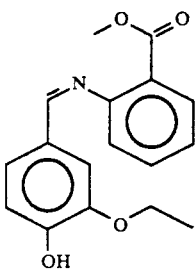

Figure 2:
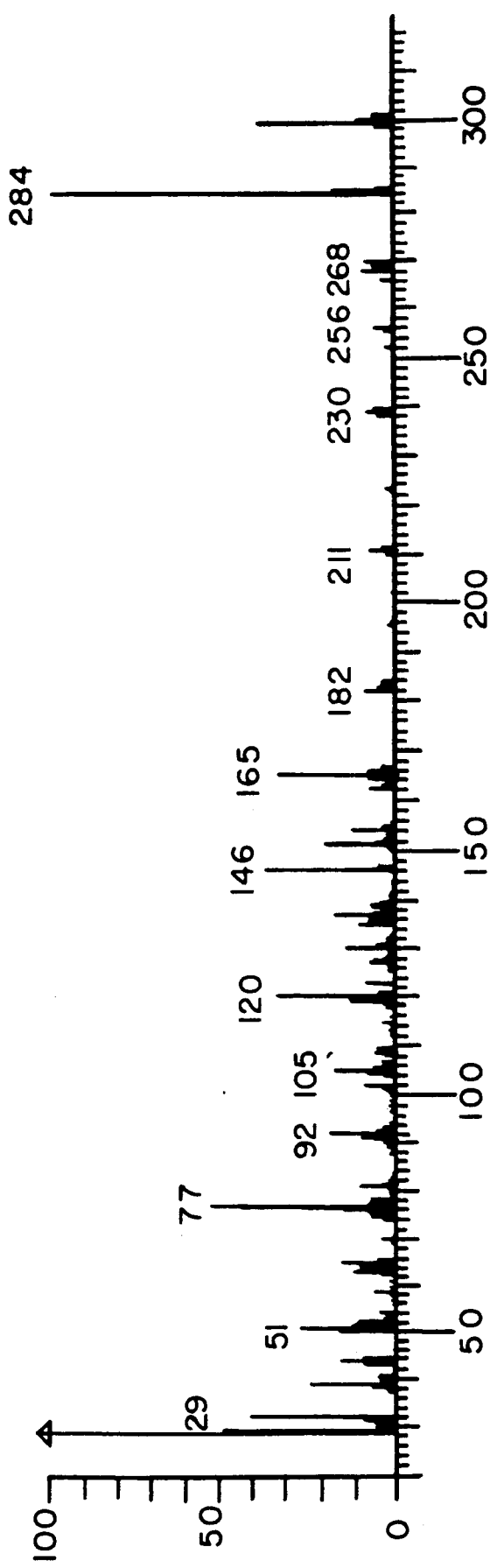

FIG. 2 is the mass spectrum for the compound having the structure:

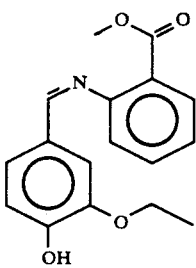

produced according to Example I.

Figure 3:
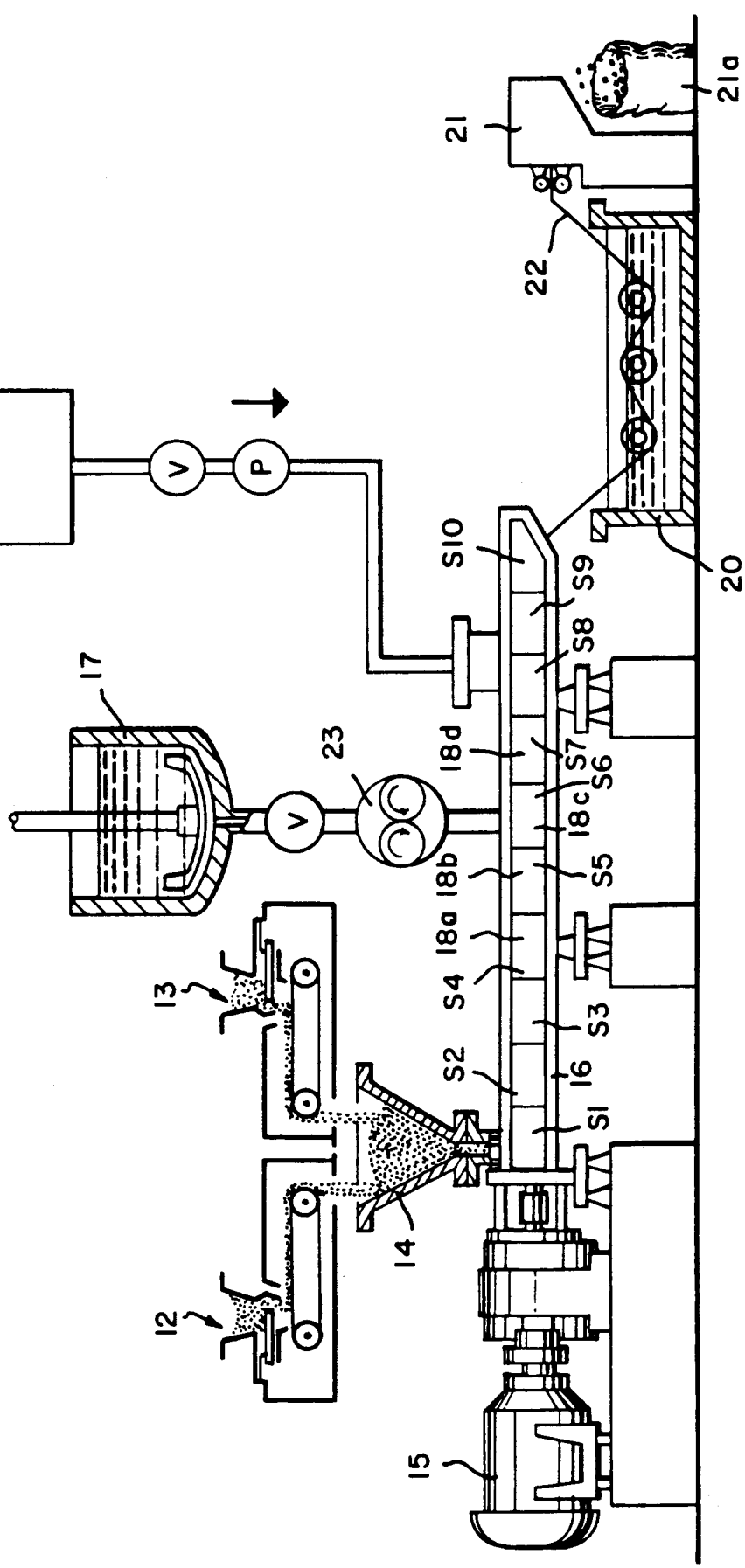

FIG. 3 is a cut-away side elevation schematic diagram of a screw extruder during the compounding of a resin with the schiff base of our invention having the structure:

while simultaneously adding foaming agent into the hollow portion of the barrel of the extruder and incorporates the pelletizing apparatus used in pelletizing the extruded foamed tow produced as a result of the extrusion operation.

FIG. 4 represents a cut-away side elevation view of apparatus used in forming perfumed polymers which contain imbedded therein the schiff base of our invention having the structure:

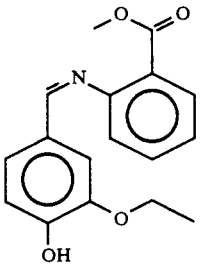

FIG. 5 is a front view of the apparatus of FIG. 4 looking in the direction of the arrows.

DETAILED DESCRIPTION OF THE DRAWINGS

Figure 1:
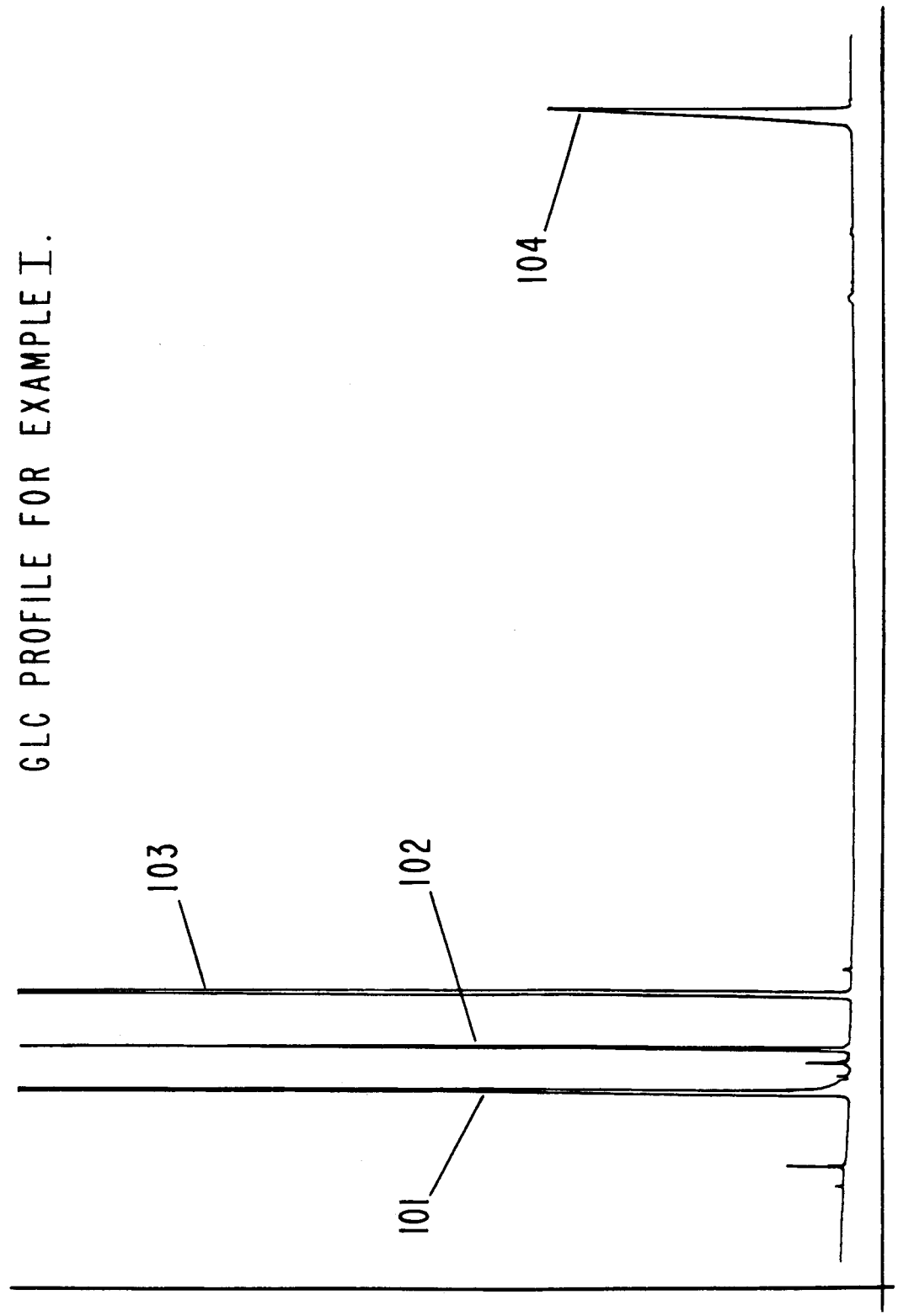
FIG. 1 is the GLC profile for the crude reaction product of Example I containing the reaction product of ethyl vanillin and methyl anthranilate, having the structure.

FIG. 1 is the GLC profile for the crude reaction product of Example I containing the compound having the structure:

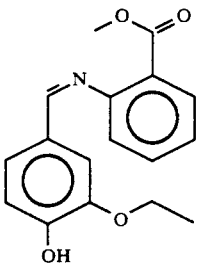

(Conditions: 50 m×0.32 mm OV-1fused silica column, programmed at 60°-220° C. at 4° C. per minute). The peak indicated by reference numeral 101 is the peak for the methyl anthranilate reactant having the structure:

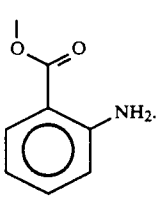

the peak indicated by reference numeral 102 is the peak for the ethyl vanillin reactant having the structure:

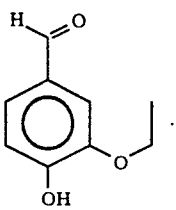

The peak indicated by reference numerals 103 is the peak for the reaction solvent, the diethyl phthalate solvent. The peak indicated by reference numeral 104 is the peak for the schiff base reaction product having the structure:

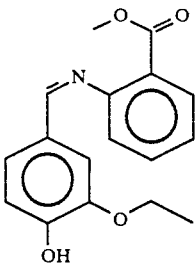

Referring to FIG. 3, FIG. 3 is a schematic cut-away elevation diagram of the extrusion and pelletizing apparatus useful in carrying out a process for incorporation of the schiff base of our invention having the structure:

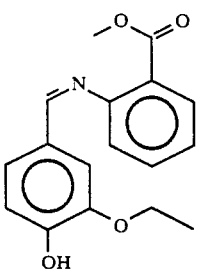

into polymers during the operation of said apparatus. Motor 15 drives the extruder screws located at 23A in barrel 16, the extruder being operated at temperatures in the range of about 150° up to about 250° C. At the beginning of the barrel, resin at source 12 together with additives, e.g., opacifiers, processing aids, colors, pearlescent agents and densifiers at location 13 is added via addition funnel 14 into the extruder. Simultaneously (when the operation reaches "steady state") the schiff base of our invention having the structure:

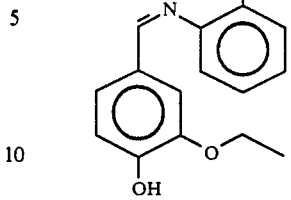

is added to the extruder at one, two or more of barrel segments 3–8 of the extruder (which may be a twin screw or single screw extruder) at locations 18a, 18b, 18c and 18d by means of gear pump 23 from source 17. From source 19 into barrel segments 5–10, the gaseous or liquid blowing agents, e.g., nitrogen, carbon dioxide and the like are added simultaneously with the addition of the schiff base of our invention having the structure:

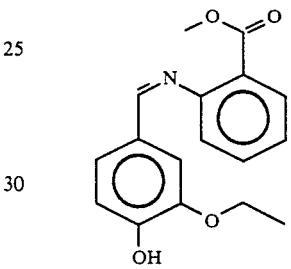

The feed rate range of the resin is about 80–300 pounds per hour. The feed rate range of the schiff base taken alone or further together with other perfumant(s) is between 1 and 45% of the feed rate range of the resin. The blowing agent rate range is such that the pressure of the gas or the pressure over the liquid being fed into the extruder is between about 50 and 200 psig. If desired, the extruded ribbon or cylinder may be passed through water bath 20 and pelletizer 21 into collection apparatus 21a.

Referring to FIGS. 4 and 5, there is provided a process for forming scented polymer pellets (wherein the polymer may be thermoplastic polymers such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 4 and 5, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other polymers or copolymers and the perfuming substance which is at least one of the schiff base having the structure:

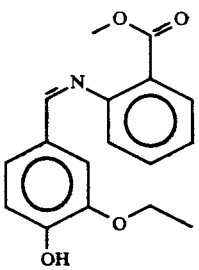

and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 20°–270° C.

Thus, the polymer or mixture of polymers added to the container 212 is heated from 10–12 hours, whereafter the perfume composition or perfume material which contains a schiff base of our invention having the structure:

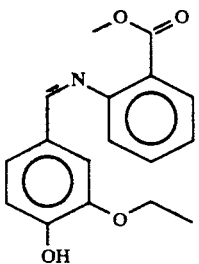

is quickly added to the melt. Generally, about 10–45 percent by weight of the resulting mixture of the perfumery substance is added to the polymer.

After the perfume material containing the schiff base of our invention is added to the container 212 the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with the schiff base of our invention having the structure:

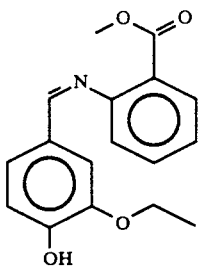

or mixture of perfume substances and the schiff base of our invention, will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance which at least contains the schiff base of our invention having the structure:

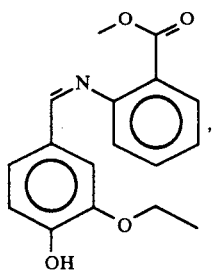

through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

Our invention provides the schiff base having the structure:

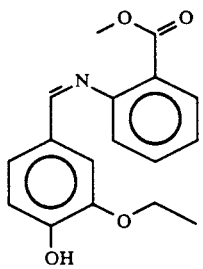

produced by means of reaction of ethyl vanillin having the structure:

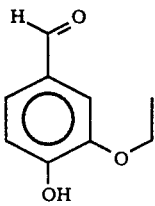

with methyl anthranilate having the structure:

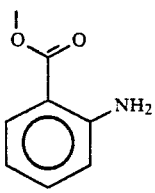

according to the reaction:

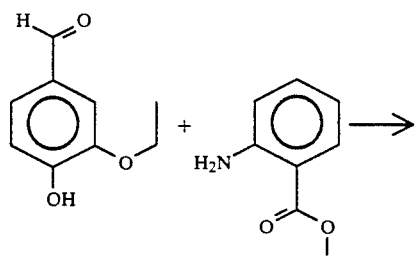

More specifically, the schiff base of our invention having the structure:

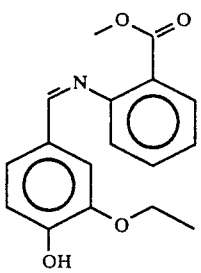

produced according to the process of our invention is capable of augmenting or enhancing or modifying the aroma characteristics of perfume compositions, colognes and perfumed articles (including soaps, anionic, cationic, nonionic or zwitterionic detergents, fabric softener compositions, optical brightener compositions and drier-added fabric softener articles) and perfumed polymers by imparting thereto an intense and surprisingly tenacious and substantive sweet, vanilla bean-like and sassafras aroma profile with sweet topnotes thus fulfilling a need in the field of perfumery and detergents and cosmetic manufacture.

The schiff base of our invention having the structure:

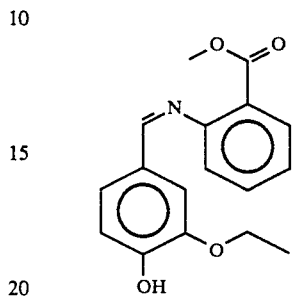

is also capable of deodorizing detergent powders suitable for use in the washing of fabrics as well as detergent powders as well as hand soaps. Such detergent powders include bleaching compositions, for example, bleaching compositions comprising a peroxy bleach compound. The schiff base of our invention having the structure:

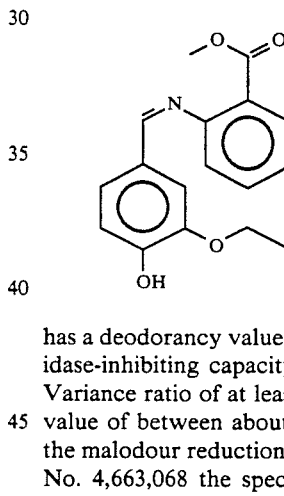

has a deodorancy value as measured by having a Lipoxidase-inhibiting capacity of at least 50% and a Raoult Variance ratio of at least 1.1 and a malodour reduction value of between about 0.25 up to 3.0 as measured by the malodour reduction value test disclosed in U.S. Pat. No. 4,663,068 the specification for which is incorporated by reference herein; and in addition, a deodorant value of from 0.50 up to 3.5 as measured by the deodorant value test as disclosed in U.S. Pat. No. 4,304,679 the specification for which is incorporated by reference herein.

The reaction to form the schiff base having the structure:

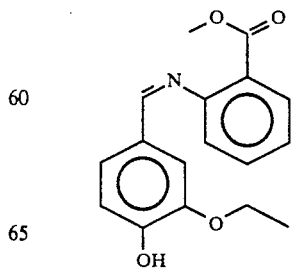

between ethyl vanillin having the structure:

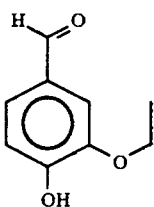

and methyl anthranilate having the structure:

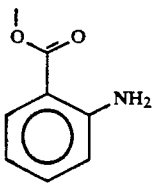

has the following parameters:
- (i) the temperature of the reaction is in the range of from about 90° C. up to about 150° C.;
- (ii) the pressure over the reaction mass may vary from about 3 mm/Hg. (vacuum) up to about 1 atmosphere with a preferable pressure of between about 5 and about 100 mm/Hg. pressure;
- (iii) the time of reaction may vary from about 3 up to about 15 hours with a preferred time of reaction of between about 6 and about 12 hours;
- (iv) the mole ratio of ethyl vanillin having the structure:

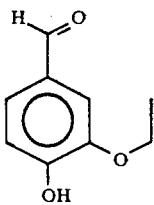

to methyl anthranilate having the structure:

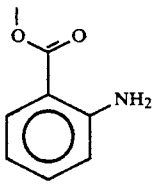

may vary from about 1:1 up to about 1.25:1 of total ethyl vanillin:methyl anthranilate with a preferred mole ratio of between about 1:1 and about 1.1:1 ethyl vanillin:methyl anthranilate.

At the end of the reaction, the reaction mass may be separated and the reaction product purified as by fractional distillation of the schiff base having the structure:

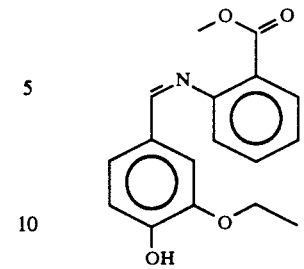

From a practical standpoint when a reaction mixture is created which gives rise to preferred perfumery properties, subsequent fractional distillation to the point of yielding an odor acceptable product is what is desired.

The schiff base having the structure:

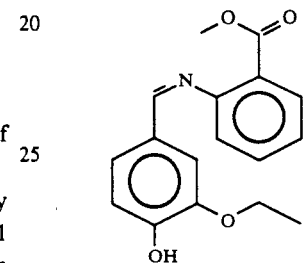

prepared in accordance with the process of our invention and one or more auxiliary perfume ingredients including, for example, alcohols, aldehydes, ketones, terpinic hydrocarbons, nitriles, esters, lactones, natural essential oils and synthetic essential oils may be admixed so that the combined odors of the individual components produce a pleasant and desired fragrance, particularly, and preferably, in floral and lavender fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the over-all sensory effect of the perfume composition will be at least the sum total of the effects of each of the ingredients. Thus, the schiff base derivative having the structure:

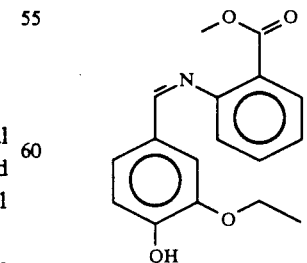

prepared in accordance with the process of our invention, can be used to alter, modify or enhance the aroma characteristics of a perfume composition, for example, by utilizing or moderating the olfactory reaction contributed by another ingredient in the composition.

The amount of schiff base derivative having the structure:

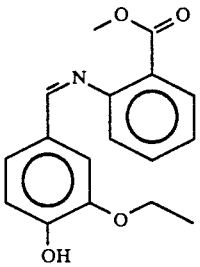

prepared in accordance with the process of our invention which will be effective in perfume compositions as well as in perfumed articles (e.g., anionic, nonionic, cationic and zwitterionic solid or liquid detergents, soaps, fabric softener compositions, drier-added fabric softener articles, optical brightener compositions, perfumed polymers and textile sizing agents) and colognes depends on many factors, including the other ingredients, their amounts and the effects which are desired. It has been found that perfume compositions containing as little as 0.01% of schiff base derivative having the structure:

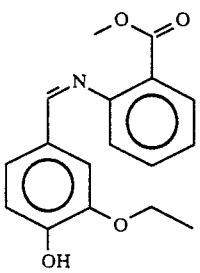

prepared in accordance with the process of our invention and less than 50% of said schiff base derivative or even less (e.g., 0.005%) can be used to impart sweet vanilla bean-like and sassafras aroma profiles with sweet topnotes to solid or liquid anionic, cationic, nonionic or zwitterionic detergents, fabric softener compositions, fabric softener articles, optical brightener compositions, textile sizing compositions, perfumed polymers or other products. The amount employed can range up to 100% of the fragrance components and will depend on considerations of cost, nature of the end product, the effect desired on the finished product and the particular fragrance sought.

The schiff base derivative having the structure:

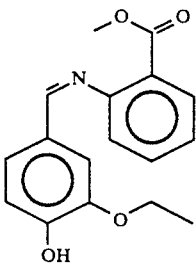

prepared in accordance with the process of our invention is useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders, and perfumed polymers and articles of manufacture produced from said perfumed polymers. When used as (an) olfactory component(s) as little as 0.2% of schiff base derivative having the structure:

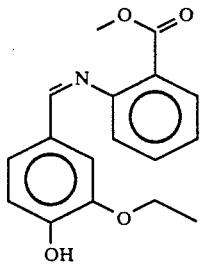

prepared in accordance with the process of our invention will suffice to impart an intense and substantive sweet vanilla bean and sassafras aroma profile with sweet topnotes to floral, rose and fresh air formulations. Generally, no more than 6% of the schiff base of our invention having the structure:

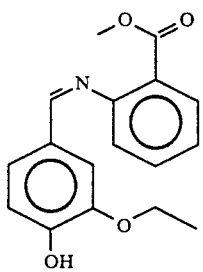

based on the ultimate end product is required in the perfumed article composition. Accordingly, the range of schiff base having the structure:

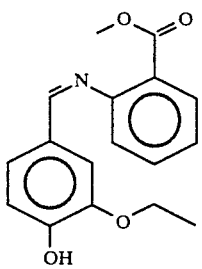

in the perfumed article is from about 0.2% by weight of the schiff base up to about 6% by weight of the schiff base based on the weight of the perfumed article.

In addition, the perfume composition of fragrance composition of our invention can contain a vehicle or carrier for the schiff base having the structure:

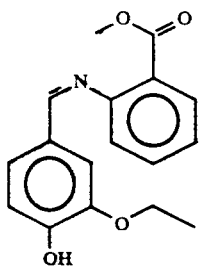

prepared in accordance with the process of our invention. The vehicle can be a liquid, such as a non-toxic alcohol, e.g., ethyl alcohol, a non-toxic glycol, e.g., propylene glycol or the like. The carrier can also be an absorbent solid, such as a gum (e.g., gum arabic, guar gum or xanthan gum) or components for encapsulating the composition (such as gelatin) as by coacervation; or such as urea-formaldehyde polymers forming a capsule shell around a liquid perfume center).

Our invention also relates to the utilization of controlled release technology for the controlled release of perfumes into gaseous environments from polymers such as mixtures of epsilon polycaprolactone polymers and polyethylene which polyepsilon caprolactone polymers are defined according to at least one of the structures:

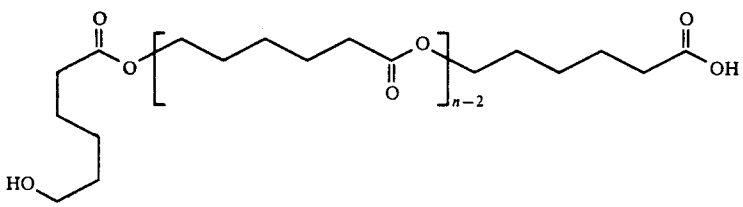

and/or

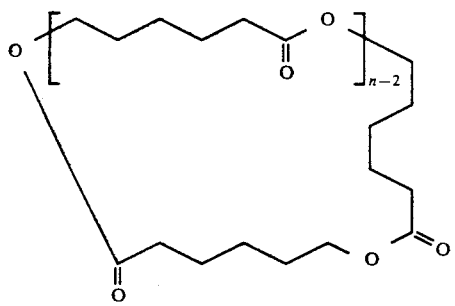

wherein "n" is from about 50 up to about 1,200 with the proviso that the average "n" in the system varies from about 150 up to about 700 according to the mathematical statement:

[700 ≧ n ≧ 150]

with the term "n" being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$\frac{dM_t}{dt} = k_1 e^{-k_2 t}$$

wherein $k_1$ and $k_2$ are constants. According to Kydonieus, "Controlled Release Technologies: Methods, Theory, and Applications" (cited, supra, the amount of perfume composition released is proportional to time as long as the concentration of perfume material present, e.g., the schiff base of our invention having the structure:

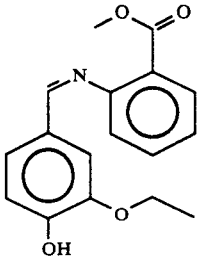

is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release constant (zero order) as long as the surface area does not change during the erosion period. This is the case with the polymers containing the schiff base of our invention having the structure:

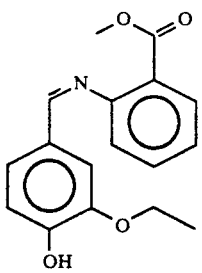

The polyepsilon caprolactone polymers useful in practicing our invention are more specifically described in the brochure of the Union Carbide Corporation, 270 Park Avenue, New York, N.Y. 10017, entitled "NEW POLYCAPROLACTONE TERMOPLASTIC POLYMERS PCL-300 AND PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone useful in conjunction with our invention against discoloration are dihydroxybenzenes such as hydroquinone or compounds having the formula:

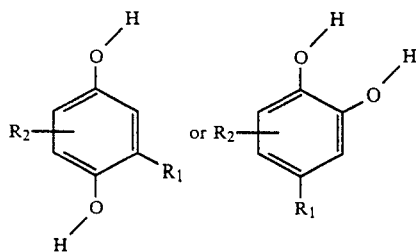

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfere with the functional fluids dissolved and/or adsorbed into the polymeric matrix.

The method of incorporating the schiff base of our invention or perfume compositions containing same into the polymers may be according to the technique of U.S. Pat. No. 3,505,432 issued on April 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylene-polyepsilon caprolactone polymer mixture (50:50) is mixed with the schiff base of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of scent is effected in two stages. In a first stage, a 50:50 (weight:weight) polyepsilon caprolactone, e.g., PCL-700: polyethylene in molten form is admixed with a high percentage of the schiff base of our invention having the structure:

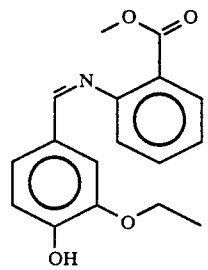

and the mixture is solidified in the form of pellets or beads. These pellets or beads thus contain a high percentage of schiff base (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention the schiff base of our invention is added to the polymer in a large closed container or drum which is maintained under controlled temperature conditions while the polymer in a melted condition is mixed with the schiff base having the structure:

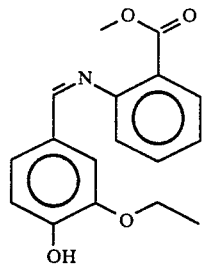

under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by the schiff base of our invention is permitted to drip through the orifices onto a continuously moving, cooled conveyor upon which the polymer containing the schiff base of our invention having the structure:

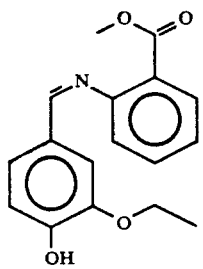

solidifies into small size pellets with the perfume imprisoned therein. The apparatus useful in conjunction with this process advantageously includes a conveyor of a material which will not adhere to the polymer which contains the schiff base of our invention.

In order that the droplets form into uniform pellets or beads, the conveyor is continuously washed with a liquid such as water to maintain the surface relatively cool. The pellets are delivered by the conveyor into a container and packaged for shipment.

The following Example I serves to illustrate a process for preparing the schiff base of our invention having the structure:

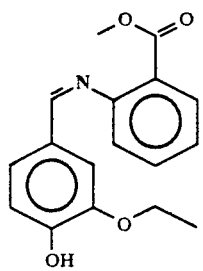

The examples following Example II are illustrative of the organoleptic utilities of the schiff base of our invention. All parts and percentages given herein are by weight unless otherwise specified.

EXAMPLE I

Preparation of Schiff Base of Methyl Anthranilate and Ethyl Vanillin

REACTION

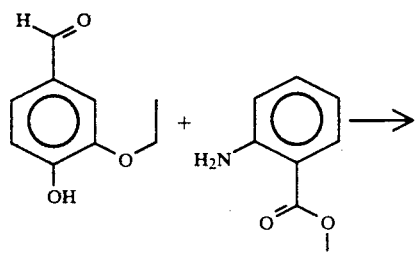

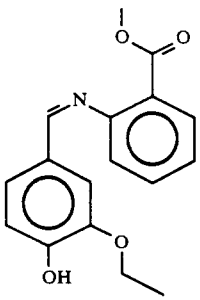

Into a 2 liter, 3 neck reaction flask equipped with stirrer, thermometer, glass "Y" adapter, 1 liter addition funnel, steam distillation head with a 45/50 bottom male joint attached to the reaction flask, head thermometer, curved fraction cutter with a 50 ml receiver, heating mantle controlled with a "Therm-O-Watch", dry ice trap, Bennert Manometer, vacuum bleed valve and vacuum pump is placed 226.5 grams of methyl anthranilate having the structure:

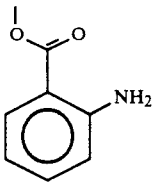

(1.5 moles).

Separately, 224.1 grams (1.35 moles) of ethyl vanillin is dissolved in diethyl phthalate (225 grams) by heating thereby forming a solution weighing approximately 500 grams.

The diethyl phthalate/ethyl vanillin solution is added to the reaction mass with stirring dropwise over a one hour period while heating the reaction mass to 50° C. at atmospheric pressure.

At the end of the addition time of the ethyl vanillin/diethyl phthalate solution, the reaction mass is placed under 50 mm/Hg. vacuum and heated to 125° C. for 3.5 hours.

After sampling for completion of reaction, the reaction is then continued for another four hours while heating at 130° C. and gradually increasing the vacuum to 30 mm/Hg. vacuum.

The resulting product (crude reaction mass) is then fractionally distilled.

FIG. 1 is the GLC profile for the reaction product (Conditions: 50 m ×0.32 mm OV-1 fused silica column programmed at 60°-220° C. at 4° C. per minute).

The peak indicated by reference numeral 101 is the peak for the methyl anthranilate having the structure:

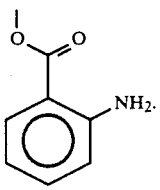

The peak indicated by reference numeral 102 is the peak for the ethyl vanillin reactant having the structure:

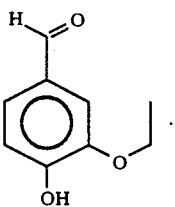

The peak indicated by reference numeral 103 is the peak for the diethyl phthalate reaction diluent.

The peak indicated by reference numeral 104 is the peak for the reaction product, the schiff base having the structure:

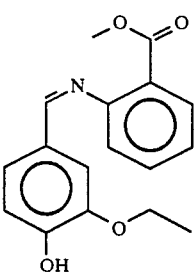

FIG. 2 is the mass spectrum after fractional distillation for the schiff base having the structure:

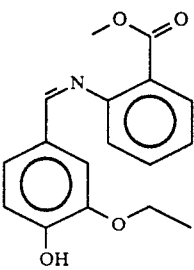

The resulting product has an excellent sweet, vanilla bean-like and sassafras aroma profile with sweep topnotes.

EXAMPLE II

Floral Perfume Compositions

The schiff base reaction product of Example I having the structure:

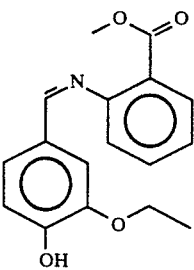

has a sweet, vanilla bean-like and sassafras aroma profile with sweet topnotes and has great warmth and richness and blends well with many floral concepts.

The following formulation is prepared:

TABLE I

| Ingredients | Parts by Weight |
|---|---|
| Citronellol | 12.3 |
| Geraniol | 2.5 |
| Amyl Cinnamic Aldehyde | 24.6 |
| Galaxolide ® 50 (Trademark for the Tricyclic Isochroman of International Flavors & Fragrances Inc.) | 9.8 |
| Vertenex High Cis (Cis-t-Butylcyclohexenyl Acetate; Para Isomer) | 7.4 |
| Rose Oxide | 0.7 |
| Cinnamic Alcohol | 19.6 |
| Aldehyde C-11 (n-Undecylenic Aldehyde) | 0.5 |
| Aldehyde C-12 (n-Dodecyl Aldehyde in 10% solution in diethyl phthalate) | 0.5 |
| Citronellal (10% solution in diethyl phthalate) | 0.5 |
| Phenyl Ethyl Acetate | 2.5 |
| Ylang Oil | 1.2 |
| Indisan (Hydrogenated derivative of reaction product of Camphene and Resorcinol) | 3.7 |
| Musk Ketone | 5.0 |
| Oakmoss Resin | 0.5 |
| Liatrix Absolute (10% in diethyl phthalate | 2.5 |
| Vetiver Acetate | 1.2 |
| Diethyl Phthalate | 5.0 |
| The schiff base having the structure: 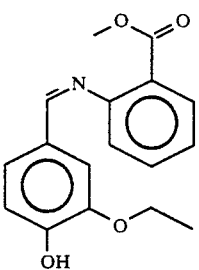 prepared according to Example I. | 5.0 |

The schiff base having the structure:

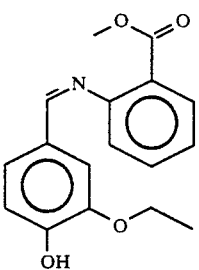

prepared according to Example I imparts sweet, vanilla bean-like and sassafras undertones with sweet topnotes to this floral fragrance formulation. Accordingly, the fragrance formulation can be described from an organoleptic standpoint as:

"floral, with sweet, vanilla bean-like and sassafras undertones and sweet topnotes".

EXAMPLE III

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The schiff base having the structure: [structure shown] prepared according to Example I. | A sweet, vanilla bean-like and sassafras aroma profile with sweet topnotes. |
| Perfume composition of Example II. | A floral, with sweet, vanilla bean-like and sassafras undertones and sweet topnotes. |

EXAMPLE IV

Perfumed Liquid Detergents

Concentrated liquid detergents (lysine salt of n-dodecylbenzene sulfonic acid as more specifically described in U.S. Pat. No. 3,948,818 issued on April 6, 1976 incorporated by reference herein) with aroma nuances as set forth in Table II of Example III are prepared containing 0.10%, 0.15%, 0.20%, 0.25%, 0.30% and 0.35% of the substance set forth in Table II of Example III. They are prepared by adding and homogeneously mixing the appropriate quantity of substance in Table II of Example III in the liquid detergent. The detergents all possess excellent aromas as set forth in Table II of Example III, the intensity increasing with greater concentrations of substance as set forth in Table II of Example III.

EXAMPLE V

Preparation of Colognes and Handkerchief Perfumes

Compositions as set forth in Table II of Example III are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example III are imparted to the colognes and to the handkerchief perfumes at all levels indicated.

EXAMPLE VI

Preparation of Soap Compositions

One hundred grams of soap chips (per sample) (IVORY ®, produced by the Procter & Gamble Company of Cincinnati, Ohio), are each mixed with one gram sample of substances as set forth in Table II of Example III until homogeneous compositions are obtained. In each of the cases, the homogeneous compositions are heated under 8 atmospheres pressure at 180° C. for a period of three hours and the resulting liquid are placed into soap molds. The resulting soap cakes, on cooling, manifest aromas as set forth in Table II of Example III.

EXAMPLE VII

Preparation of Solid Detergent Compositions

Detergents are prepared using the following ingredients according to Example I of Canadian Patent No. 1,007,948 (incorporated herein by reference):

| Ingredient | Percent by Weight |
|---|---|
| NEODOL ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table II of Example III. Each of the detergent samples has an excellent aroma as indicated in Table II of Example III.

EXAMPLE VIII

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.);
   57% $C_{20-22}$ HAPS
   22% isopropyl alcohol
   20% antistatic agent
   1% of one of the substances as set forth in Table II of Example III.

Fabric softening compositions prepared according to Example I at column 15 of U.S. Pat. No. 3,632,396 having aroma characteristics as set forth in Table II of Example III, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example III is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example III, supra.

EXAMPLE IX

Hair Spray Formulations

The following hair spray formulation is prepared by first dissolving PVP/VA E-735 copolymer manufactured by the GAF Corporation of 140 West 51st Sreet, New York, N.Y., in 91.62 grams of 95% food grade ethanol. 8.0 Grams of the polymer is dissolved in the alcohol. The following ingredients are added to the PVP/VA alcoholic solution:

| Ingredients | Weight Percent |
| --- | --- |
| Dioctyl sebacate | 0.05 |
| Benzyl alcohol | 0.10 |
| Dow Corning 473 fluid (prepared by the Dow Corning Corporation) | 0.10 |
| Tween 20 surfactant prepared by ICI America Corporation) | 0.03 |
| One of the perfumery substances as set forth in Table II of Example III, supra. | 0.10 |

The perfume substances as set forth in Table II of Example III add aroma characteristics as set forth in Table II of Example III which are rather intense and aesthetically pleasing to the users of the soft-feel, good-hold pump hair sprays.

EXAMPLE X

Conditioning Shampoos

Monamid CMA (prepared by the Mona Industries Company)(3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" & "COMPOSITION B" are then mixed in a 50:50 weight ratio of A:B and cooled to 45° C. and 0.3 weight percent of perfuming substance as set forth in Table II of Example III is added to the mixture. The resulting mixture is cooled to 40° C. and blending is carried out for an additional one hour in each case. At the end of the blending period, the resulting material has a pleasant fragrance as indicated in Table II of Example III.

EXAMPLE XI

Each of the fragrance materials of Table II of Example III, supra, are added to a 50:50 weight:weight mixture of low density polyethylene:polyepsilon caprolactone PCL-700 forming pellets with scents as set forth in Table II of Example III, supra.

75 Pounds of a 50:50 mixture of PCL-700 polyepsilon caprolactone (manufactured by the Union Carbide Corporation of New York, New York having a melting point of about 180°-190° F.):Low density polyethylene, are heated to about 250° F. in a container of the kind illustrated in FIGS. 20 and 21. 25 Pounds of each of the fragrance materials as set forth in Table II of Example III, is then quickly added to the liquified polymer mixture, the lid 228 is put in place and the agitating means 273 are actuated. The temperature is then raised to about 260° F. and the mixing is continued for 5-15 minutes. The valve "V" is then opened to allow flow of the molten polymer enriched with perfume ingredient to exit through the orifices 234. The liquid falling through the orifices 234 solidifies almost instantaneously upon impact with the moving cooled conveyor 238. Polymer beads or pellets 244 having pronounced scents as described in Table II of Example III, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table II of Example III, supra. The sheets of films are cut into strips of 0.25" in width ×3" in length and placed into room air fresheners.

On operation of the room air freshener, after four minutes, the room in each case has an aesthetically pleasing aroma with no foul odor being present, the aroma being described in Table II of Example III, supra.

EXAMPLE XI

A fabric washing deodorant detergent powder product is prepared by admixing the following ingredients:

| Ingredients | Parts by Weight |
| --- | --- |
| Linear alkylbenzene sulfonate | 9.0 |
| $C_{13}$-$C_{15}$ straight chain alcohols (30:30:40 mixture of $C_{13}$, $C_{14}$, and $C_{15}$ straight chain alcohol) | 4.0 |
| Sodium tripolyphosphate | 16.0 |
| ZEAOLIGHT | 8.0 |
| Sodium silicate | 4.0 |
| Magnesium silicate | 0.8 |
| Ethylene diamine | 0.6 |
| N,N,N',N'-[tetra(methylene phosphonic acid)] sodium carboxy methyl cellulose | 0.9 |
| Anti-foam | 1.5 |
| Sodium Perborate tetrahydrate | 14.0 |
| N,N,N',N'-Tetraacetyl Glycoluril | 4.2 |
| The schiff base reaction product of ethyl vanillin and methyl antranilate produced according to Example I having the structure: | 0.35 |

-continued

| Ingredients | Parts by Weight |
|---|---|
| 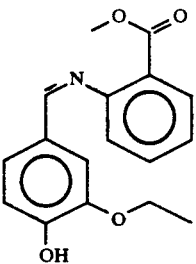 | |
| Water | 45.0 |
| Sodium sulfate | 5.0 |

The resulting fabric washing deodorant detergent powder on use gives rise to a very pleasant "fresh air" aroma without any aesthetically displeasing aromas subsequent to washing of fabrics in the standard washing machine cycle.

Deodorant detergent products have also been prepared according to Examples I-IX of U.S. Pat. No. 4,304,679 incorporated by reference herein.

Thus, exemplified herein by reference are the following:

(a) a deodorant detergent product comprising:
(i) from 0.5 to 99.99% by weight of a non-soap detergent active compound; and
(ii) from 0.01 to 10% by weight of a deodorant composition comprising from 45 to 100% by weight of the schiff base of our invention having the structure:

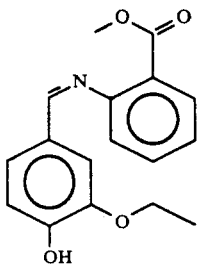

said schiff base having a lipoxidase-inhibiting capacity of at least 50% or a Raoult variance ratio of at least 1.1 as stated in said U.S. Pat. No. 4,304,679, with the schiff base composition having the structure:

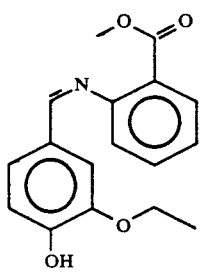

having a deodorant value of from 0.5 to 3.5 as measured by the deodorant value test as specifically set forth in said U.S. Pat. No. 4,304,679 and exemplified therein.

Furthermore, the examples of U.S. Pat. No. 4,663,068 are also incorporated herein by reference.

Thus, exemplified herein are detergent powder products suitable for the washing of fabrics comprising:
(i) from 5 to 40% by weight of a non-soap detergent active compound comprising an anionic detergent active compound;
(ii) from 1 to 90% of a non-soap detergency builder;
(iii) from 1 to 30% by weight a peroxy bleach compound together with an activator therefor;
(iv) from 0.1 up to 10% by weight of a bleach stable perfume which comprises 50-100% by weight of the bleach stable schiff base having the structure:

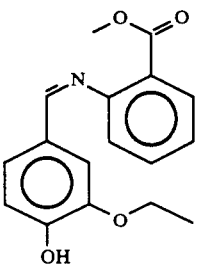

having a Lipoxidase-inhibiting capacity of at least 50% or a Raoult variance ratio of at least 1.1 as defined according to U.S. Pat. No. 4,663,068 incorporated by reference herein, with the schiff base being stable in the presence of sodium perborate tetrahydrate or any other alkali metal perborate tetrahydrate and N,N,N',N'-tetraacetyl ethylenediamine (TEAD) according to the bleach stability test as defined in said U.S. Pat. No. 4,663,068 incorporated by reference herein, the bleach stable deodorant schiff base having a Malodor Reduction Value of from 0.25 up to 3.0 as measured by the Malodor Reduction Value test defined in said U.S. Pat. No. No. 4,663,068 incorporated by reference herein.

The peroxy bleach activator may be exemplified by the following peroxy bleach activators:
N,N,N',N'-tetracetyl ethylenediamine;
N,N,N',N'-tetracetyl glycoluril;
Glucose pentaacetate;
Sodium acetoxybenzene sulphonate;
Sodium nonanoyloxybenzene sulphonate;
Sodium octanoyloxybenzene sulphonate; and
mixtures thereof.

The non-soap anionic detergent active compound may be selected from the group consisting of sodium and potassium alkyl sulphates, sodium potassium and ammonium alkyl benzene sulphonates, sodium alkyl glyceryl ether sulphates, sodium coconut oil fatty acids monoglyceride sulphates and sulphonates, sodium and potassium salts of sulphuric acid esters of higher ($C_9$–$C_{18}$) fatty alcohol-alkylene oxide, the reaction products of fatty acids esterified with isethionic acid and neutralized with sodium hydroxide, sodium and potassium salts of fatty acid amides of methyl taurine, alkane monosulphonates, olefin sulphonates and mixtures thereof.

The nonionic detergent active compound may be selected from the group consisting of reaction products of alkylene oxides with alkyl ($C_6$–$C_{22}$) phenols, the condensation products of aliphatic ($C_8$–$C_{18}$) primary or secondary linear or branched alcohols with ethylene oxide, products made by condensation of ethylene oxide with the reaction products of propylene oxide and ethylene diamine, long-chain tertiary amine oxides, long-chain phosphine oxides and dialkyl sulphoxides and mixtures thereof.

What is claimed is:

1. A schiff base reaction product produced according to the process of reacting methyl anthranilate having the structure:

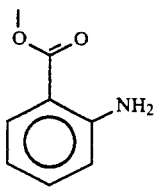

with ethyl vanillin having the structure:

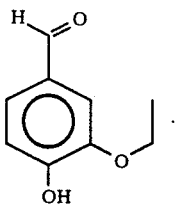

2. A schiff base reaction product having the structure:

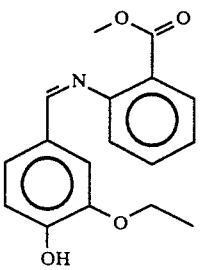

* * * * *